(12) United States Patent
Döbelin

(10) Patent No.: US 6,482,363 B1
(45) Date of Patent: Nov. 19, 2002

(54) FEED SYSTEM FOR CLOSED REACTION CHAMBERS WITH MOVEABLE SAMPLE RACKS

(75) Inventor: Werner Döbelin, Reinach (CH)

(73) Assignee: Hettlab AG, Bach (CH)

( * ) Notice: Subject to any disclaimer, the term of this patent is extended or adjusted under 35 U.S.C. 154(b) by 0 days.

(21) Appl. No.: 09/830,943

(22) PCT Filed: Nov. 3, 1999

(86) PCT No.: PCT/CH99/00516
§ 371 (c)(1),
(2), (4) Date: May 2, 2001

(87) PCT Pub. No.: WO00/25925
PCT Pub. Date: May 11, 2000

(30) Foreign Application Priority Data

Nov. 3, 1998 (CH) .............................................. 2214/98

(51) Int. Cl.[7] .............................................. B01F 15/02
(52) U.S. Cl. ........................ 422/100; 366/208; 366/219; 366/177.1
(58) Field of Search ............................. 366/139, 177.1, 366/180.1, 181.6, 198, 208, 209, 218, 219, 237, 240; 422/100

(56) References Cited

U.S. PATENT DOCUMENTS

| | | | | |
|---|---|---|---|---|
| 3,167,259 A | * | 1/1965 | Pitchford | 366/237 |
| 4,058,146 A | * | 11/1977 | Citrin | 422/100 |
| 5,055,263 A | * | 10/1991 | Meltzer | 422/100 |
| 5,121,991 A | * | 6/1992 | Wakatake | 366/208 |
| 5,132,088 A | * | 7/1992 | Wakatake | 422/100 |
| 6,274,094 B1 | * | 8/2001 | Weller et al. | 422/100 |

FOREIGN PATENT DOCUMENTS

| | | |
|---|---|---|
| EP | 0210014 | 1/1987 |
| WO | WO9002604 | 3/1990 |
| WO | WO9820965 | 5/1998 |

* cited by examiner

Primary Examiner—Tony G. Soohoo
(74) Attorney, Agent, or Firm—Ladas & Parry

(57) ABSTRACT

The invention relates to a system that feeds gaseous or liquid media into moveable sample vessels or reaction vessels in vacuum centrifuges or reaction chambers that are provided with an integrated shaker. An adapter plate fitted with needles that are allocated to individual vessels is arranged inside the centrifuge or reaction chamber above the sample vessels. The adapter plate is provided with a system for the introduction of the gaseous or liquid medium. The height of the adapter plate can be adjusted. This enables the depth at which the needles are introduced into the sample vessels to be chosen at will.

5 Claims, 1 Drawing Sheet

FEED SYSTEM FOR CLOSED REACTION CHAMBERS WITH MOVEABLE SAMPLE RACKS

BACKGROUND OF THE INVENTION

The invention relates to a system that feeds gaseous or liquid media into a number of moveable sample vessels or reaction vessels on a rotor in vacuum centrifuges or on an integrated shaker plate in reaction chambers, for simultaneous processing of the samples contained therein, with an adapter plate of adjustable height being arranged inside the centrifuge or reaction chamber above the sample vessels or reaction vessels, with needles that are allocated to the individual sample vessels or reaction vessels being arranged on said adapter plate, and with a system for the introduction of gaseous or liquid media.

The processing of samples in vacuum centrifuges and reaction chambers creates problems which have not yet been solved satisfactorily.

The samples are usually in test tubes or racks with appropriate recesses. As these sample vessels are very narrow, i.e. the ratio of vessel depth to vessel diameter is very large, the following problem arises: the cooling of the sample due to evaporation makes the neck of the sample vessel cold and thereby substantially prevents vapour phase from being sucked out of the sample vessels.

A device in which the sample vessels are placed in preheated or heated racks is known from PCT/CH 97/00431 and vacuum centrifuges. As the cooling due to the energy of vaporization can only be very poorly compensated by heating or IR radiation, and the sample vessels are usually made of a well insulated material such as glass or plastic, it has to be accepted that certain applications will involve extremely tedious processes.

EP-A-0 210 014 describes a sample treatment system equipped with a device for washing the sample vessels. The washing device has needles which are arranged in a washing block and allocated to individual sample vessels. The washing block is part of a multi-functional and so-called integrated transfer head. The washing block can be moved vertically in order to introduce the needles into the sample vessels. However, this system would be unsuitable for use together with sample vessels that move sideways during processing because the washing block is incapable of lateral movement.

WO 90 02605 A describes an apparatus for peptide synthesis which has a liquid feed system, for example for washing the reaction chambers. The liquid feed system can be moved away from the reaction chambers when it is not needed. Again, this liquid feed system is unsuitable for use with sample vessels that move sideways because it is incapable of lateral movement.

SUMMARY OF THE INVENTION

The object of the invention is to provide a system which overcomes said disadvantages of the state of the art.

According to the invention, this object is achieved by a feed system of the type mentioned at the outset, which is characterized in that the adapter plate is rigidly connected to the rotor or the shaker plate in its direction of motion in such a way that the needles can be introduced into the sample vessels while the rotor or the shaker plate is moving.

This system makes it possible to introduce warm gas or liquid into the moveable sample vessels in order to prevent the neck of the sample vessel from becoming cold during the evaporation process and to enable reagents to be introduced simultaneously into the individual sample vessels.

The adapter plate and the sample rack, or the rotor in the case of a centrifuge, are coupled together so that the position of the needle in the corresponding sample vessel remains unchanged during shaking or centrifugation. Preferably, the adapter plate can be heated so that the medium is preheated when it flows into the sample vessels. In the case of systems used in vacuum evaporators, the flow rate of the preferably inert gas is reduced so as at least to prevent the neck of the sample vessel from becoming cold. The faster the gas flow, the more powerful the vacuum system has to be in order to maintain the desired vacuum in the reaction chamber.

Operating this device under pressure demands an appropriate pressure-resistant reaction chamber designed according to the state of the art as described in PCT/CH 97/00431.

DESCRIPTION OF THE PRESENT INVENTION

Figure 1:
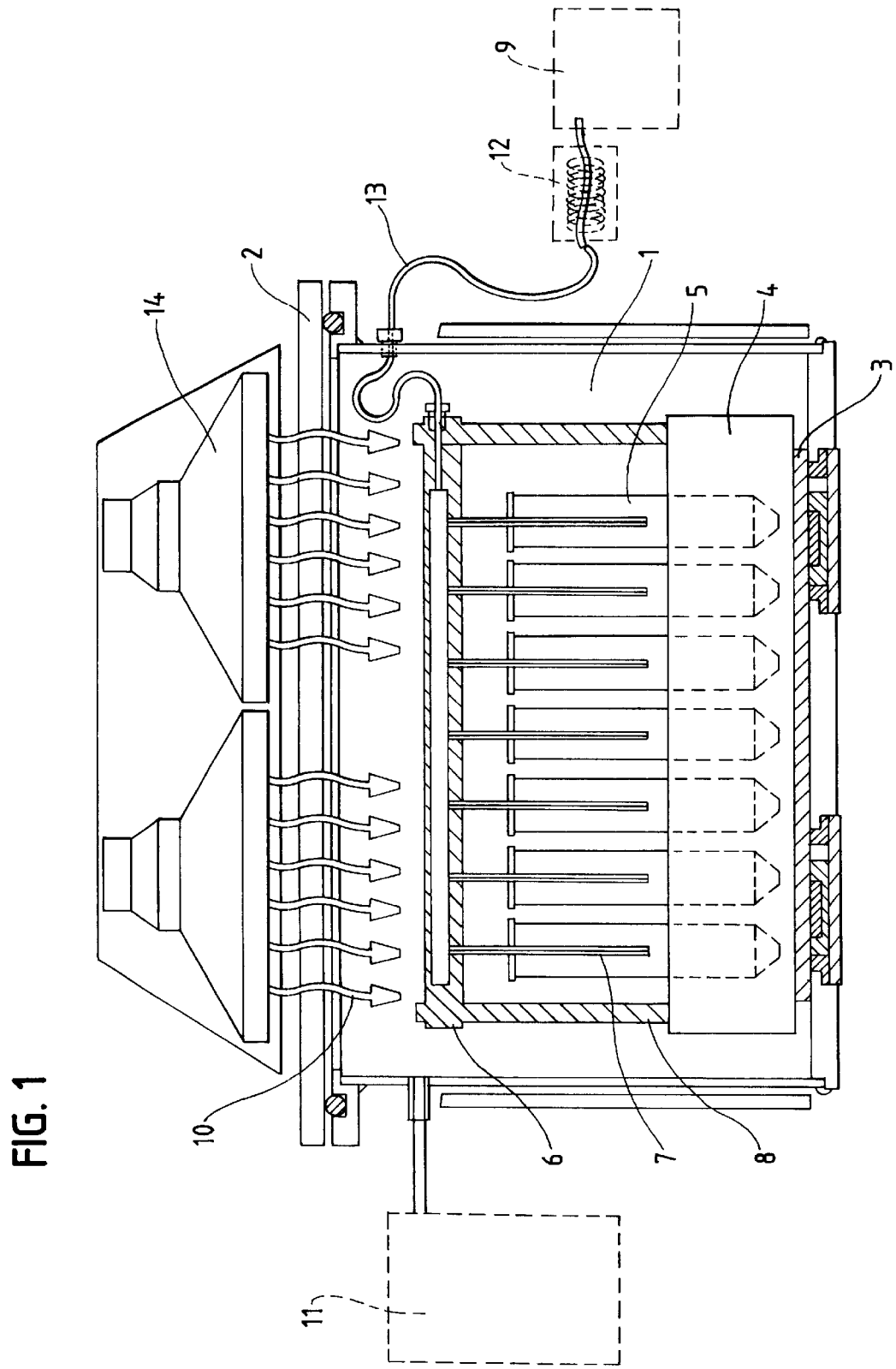
FIG. 1 is a side view of a preferred embodiment of the invention.

A preferred embodiment is illustrated in the following description with the help of the attached drawing:

As shown in the drawing, a reaction chamber 1 is closed at the top by a glass plate 2. The reaction chamber accommodates a shaker plate 3 on which a sample rack 4 with sample vessels 5 is placed. An adapter plate 6 with needles 7 is located above the sample rack 4 and is fixed to guide pegs 8 firmly connected to the shaker plate. The adapter plate 6 thus moves synchronously with the shaker plate 3 and the sample rack 4. Via a gas introduction system 9 and a flexible transfer line 13, gas flows through a heat exchanger 12 into the adapter plate 6, which can be heated by means of infrared lamps 10 arranged above the glass plate outside the reaction chamber. The gas flows through the adapter plate 6, warms up and flows through the needles 7 into the sample vessels 5. The gas or vapours are sucked out of the reaction chamber 1 via the vacuum pump system 11.

Suitable needles are glass, metal or plastic capillaries or, in the case of centrifuges with outward-swinging sample vessels, flexible fused silica, Teflon or plastic capillaries.

In vacuum centrifuges in which the adapter plate and the capillaries rotate together with the sample vessels, the gas introduction system is connected at the centre of the adapter plate by means of sealing systems known per se.

The gas introduction system, the vacuum pump system and the reaction chamber with heat radiators are known per se in the relevant state of the art and do not therefore need to be described in greater detail here.

Of course, by adapting the apparatus accordingly, gas can also be introduced under pressure. The reaction chamber and gas introduction system are designed for the required pressure range according to the appropriate state of the art.

What is claimed is:

1. System that feeds gaseous or liquid media into a number of movable sample vessels or reaction vessels on a rotor in vacuum centrifuges or on an integrated shaker plate in reaction chambers, for simultaneous processing of the samples contained therein, with an adapted plate of adjustable height being arranged inside the centrifuge or reaction chamber above the sample vessels or reaction vessels, with needles that are allocated to the individual sample vessels or reaction vessels being arranged on said adapter plate, and with a system for the introduction of gaseous or liquid media, wherein the adapter plate is rigidly connected to the rotor or the shaker plate in its direction of motion in such a way that the needles can be introduced into the sample vessels while the rotor or the shaker plate is moving.

2. Feed system according to claim 1, wherein a vacuum pump is connected to the centrifuge or reaction chamber and maintains a vacuum in the centrifuge or reaction chamber during the introduction of gaseous medium.

3. Feed system according to claim 1 or 2, wherein the introduction system is provided with a heating device.

4. Feed system according to claim 1 or 2, wherein the introduction system is provided with a heat exchanger and a flexible transfer line arranged outside the reaction chamber.

5. Use of a feed system according to claim 1, in evaporators or in reaction chambers for chemical synthesis.

* * * * *